(12) United States Patent
Aubrun-Sonneville

(10) Patent No.: US 7,811,953 B2
(45) Date of Patent: Oct. 12, 2010

(54) SOLUBLE PATCH

(75) Inventor: Odile Aubrun-Sonneville, Antony (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/169,779

(22) Filed: Jul. 9, 2008

(65) Prior Publication Data

US 2008/0269095 A1 Oct. 30, 2008

Related U.S. Application Data

(63) Continuation of application No. 11/567,336, filed on Dec. 6, 2006, now abandoned.

(60) Provisional application No. 60/752,051, filed on Dec. 21, 2005.

(30) Foreign Application Priority Data

Dec. 7, 2005 (FR) .................................. 05 53752

(51) Int. Cl.
*B32B 27/02* (2006.01)
*D04H 1/00* (2006.01)

(52) U.S. Cl. ........................ 442/166; 442/164; 442/414

(58) Field of Classification Search ................. 442/414, 442/164, 166
See application file for complete search history.

(56) References Cited

U.S. PATENT DOCUMENTS

| 4,416,791 | A | 11/1983 | Haq |
| 6,399,668 | B1 | 6/2002 | Miyake et al. |
| 2007/0134304 | A1* | 6/2007 | Aubrun-Sonneville et al. ... 424/443 |

FOREIGN PATENT DOCUMENTS

| EP | 0 750 905 | 1/1997 |
| WO | WO 02/05789 | 1/2002 |
| WO | WO 2005/003423 | 1/2005 |

* cited by examiner

*Primary Examiner*—Lynda Salvatore
(74) *Attorney, Agent, or Firm*—Oblon, Spivak, McClelland, Maier & Neustadt, L.L.P.

(57) ABSTRACT

An article, preferably a patch, containing:
a support in the form of at least one sheet containing fibres that are water-soluble at a temperature of 0-30° C., and
a composition carried by the support, containing at least one water-soluble gelling agent which swells in less than 30 seconds in water at a temperature of 20° C. to 30° C.

19 Claims, No Drawings

SOLUBLE PATCH

REFERENCE TO PRIOR APPLICATIONS

This application is a continuation of U.S. Ser. No. 11/567,336 filed Dec. 6, 2006, abandoned and claims priority to U.S. provisional application 60/752,051 filed Dec. 21, 2005, and to French patent application 0553752 filed Dec. 7, 2005, both incorporated herein by reference.

FIELD OF THE INVENTION

The present invention relates to articles of manufacture such as patches that comprise a water-soluble support and a composition carried by the support, and to the uses thereof, in particular in the cosmetics field.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

In the cosmetics field, it is known practice to use cosmetic patches that consist of a water-insoluble support impregnated with a cosmetic composition. A patch is, by definition, applied to a limited area of skin, the area being more or less large, which allows the slow release of an active substance by transdermal effect, and thus the effective treatment of specific areas. However, insoluble-support patches have the drawback, firstly, of generating waste to be eliminated and, secondly, of being able to perform only one function and of not being modulatable according to the desired aim, contributing to an increase in the number of products to be used in routine care. Now, it may be advantageous to have products that can have two functions depending on the method of application, for example a foaming cleansing product that can be used daily, but that can also be used weekly as a specific treatment with a leave-on time for greater effective-ness.

Moreover, water-soluble thin films containing active agents have been described, which films are moistened with water to give a composition (solution, dispersion or emulsion) that is then spread on the skin. Document WO-A-02/05789 describes, for example, such films. However, these films have the drawback of being complex to manufacture, with solubilization of the components, heating and drying in order to obtain a dry film. In addition, they are difficult to dry if they are too thick, and they are fragile and difficult to handle if the size is too great.

SUMMARY OF THE INVENTION

There remains therefore the need to have articles of manufacture, including patches, that do not have the drawbacks of those of the prior art, and in particular to have rinse-off or wipe-off articles that can have several functions, for example that can be used, as required by users, as a patch or care product, that can constitute, for example, a daily product to be used diluted, or a weekly product to be used on a defined area with a leave-on time.

The present application satisfies this need. Specifically, the inventor has found, surprisingly, that it is possible to prepare articles comprising a support containing soluble fibres and a specific gelling agent, and to obtain, by dissolution of these articles in water or in an aqueous medium, a gelled composition for example, in particular a gelled cosmetic composition that has good cosmetic properties and that can constitute a patch.

The use of articles of this type makes it possible to lift the constraints of formulation in so far as these articles can produce a large range of products, from gels to creams, for various applications, according to the composition applied to the support.

DETAILED DESCRIPTION OF THE PREFERRED EMBODIMENTS

Thus, according to one of its aspects, the invention discloses a cosmetic or dermatological article, comprising:
- a support in the form of at least one sheet comprising fibres that are water-soluble at a temperature less than or equal to 30° C., and
- a composition carried by the support, containing at least one water-soluble gelling agent which swells in less than 30 seconds in water at a temperature of 20° C. to 30° C.

The expression "cosmetic or dermatological article" means a cosmetic or dermatological product comprising a solid support including a composition carried by this support. This article may constitute especially a patch to be wetted and applied on the skin.

In the present application, the expression "carried by the support" means that the composition may be either placed on the support or introduced into the cavity formed by the support when the latter comprises at least two supports (e.g., sheets) forming a cavity. Of course, both situations may occur in the same article depending on the extent of overlap of the at least two supports. "On the support" includes composition located in interstices of the support.

The expression "temperature less than or equal to 30° C." means a temperature that does not exceed 30° C. but is not less than 0° C., e.g., 0-30° C., for example ranging from more than 0° C. to 30° C., better still from 5° C. to 30° C., and even better still from 10° C. to 30° C., including 15, 20 and 25° C., and all ranges and subranges therebetween.

The expression "gelling agent which swells in less than 30 seconds in water at a temperature of 20° C. to 30° C." means a gelling agent which swells rapidly after being introduced into 20° C. to 30° C. water at a concentration of 5 to 50% by weight.

When used, the gelling agent(s) used according to the invention will preferably swell rapidly in water so as to form a material that does not run and that can thus be readily applied to the area to be treated.

The presence of the water-soluble gelling agent allows the article to be converted to a more or less smooth gel or paste, for example after a contact time of less than 30 minutes with a small amount of water at ambient temperature (20 to 30° C.), so as to be able to be used in particular as a rinse-off patch to be applied locally (for example, on the area of the nose or of the forehead) with a leave-on time for a stronger action, or as a product to be applied to a more extensive area (for example, the entire face), a multifunctional article according to the needs of the user. The term "multifunctional article" means an article which, as required by the user, can be employed differently, for example as a patch in a limited area or as a cleansing product in a larger area. In the case of the patch, the article is simply moistened so as to obtain a thick gel. In the case of the cleansing product, the article can be solubilized in a larger amount of water so as to obtain a product that is easier to spread and less concentrated in terms of active agent for treating a widespread area.

For example, the article can constitute a patch for greasy skin for the nose, to be used once a week, allowing a targeted treatment with keratolytic and/or antibacterial active agents; the patch is moistened before use, it is left on for a few minutes (for example 10 minutes), then it is subsequently rinsed off and/or wiped off. Before rinsing or wiping, it can also be spread on the remainder of the face, possibly by adding water, so as to treat or cleanse the entire face with a less concentrated formula.

The article according to the invention can also constitute a formula to be rehydrated before use with an amount of water to be adjusted by the consumer depending on the desired texture or the desired activity.

Preferably, this article constitutes a soluble or partially soluble patch. The term "partially soluble" means that the article comprises a support comprising at least 60% by weight of water-soluble fibres relative to the total weight of fibres.

The terms "sheet" and "layer" are synonyms in the present application. The support of the present invention is preferably in the form of one or more sheets of fibres, which is different from the water-soluble thin films which are not in the form of sheets of fibres. Compared with these water-soluble thin films, the supports based on water-soluble fibre sheets according to the invention have the advantage of allowing the incorporation of incompatible constituents, and being simpler to use since they do not require any premixing or solubilization of the components, nor heating to evaporate off the solvent, the process also being more rapid and less expensive. In addition, the supports according to the invention have the advantage of allowing a greater diversity in the choice of the shape and the appearance of the article since the fibre sheet can vary in thickness and density providing the opportunity for a great variety of size and shape, whereas the thin film is difficult to dry if it is too thick, and it is fragile and difficult to handle if the size is too great.

According to a preferred embodiment of the invention, the article is in the form of at least two sheets that together define a cavity, at least one of the sheets comprising fibres that are water-soluble at a temperature less than or equal to 30° C.,
  the cavity containing a composition containing a water-soluble gelling agent which swells in less than 30 seconds in water at a temperature of 20° C. to 30° C.

The two sheets are preferably assembled at their periphery and thus form a cavity for introducing the composition containing the water-soluble gelling agent.

The sheets can be formed entirely of water-soluble fibres or else one of the sheets can consist entirely of water-soluble fibres and the other sheet can consist of insoluble fibres or of both water-soluble fibres and water-insoluble fibres, or else the two sheets can consist of both soluble fibres and insoluble fibres.

According to a specific preferred embodiment of the invention, at least one of the sheets consists exclusively of water-soluble fibres.

A gelled composition for topical application, in particular a cosmetic or dermatological composition, is obtained by moistening or dissolving the article according to the invention in water or in an aqueous composition.

Thus, a subject of the invention, according to another of its aspects, is also a composition for topical application, obtained by dissolving, in water, an article as defined above, i.e. a composition obtained by dissolving a support in the form of at least one sheet comprising fibres that are water-soluble at a temperature less than or equal to 30° C., said support carrying at least one water-soluble gelling agent which swells in less than 30 seconds in water at a temperature of 20° C. to 30° C. This composition may be obtained from a support comprising one or more layers of fibres. The temperature for dissolving the article in water is generally ambient temperature (20 to 30° C.), but may be above ambient temperature if desired, depending on the use envisaged.

A subject of the invention, according to another of its aspects, is also a cosmetic process for treating keratin materials such as the skin, the hair, the mucous membranes and the integuments, and in particular for treating the skin, comprising:
  the formation of a cosmetic composition by dissolving, in water, a support comprising at least one sheet comprising fibres that are water-soluble at a temperature less than or equal to 30° C., and carrying at least one water-soluble gelling agent which swells in less than 30 seconds in water at a temperature of 20° C. to 30° C.,
  the application of the composition thus formed to the keratin materials.

The cosmetic treatment may in particular be skin care.

The expression "water-soluble at a temperature less than or equal to 30° C." should be understood to mean solubilization in water at a temperature ranging up to 30° C. with the aid of manual agitation and/or friction of the support, where appropriate, for a period of time typically less than 5 min, preferably less than 1 min, preferably less than 30 seconds. The invention does not exclude water at a temperature above 30° C. being used to dissolve the support.

Since the article according to the invention is intended for topical application, it preferably comprises a physiologically acceptable medium. The term "physiologically acceptable medium" means a medium compatible with keratin materials such as the skin, the lips, the nails, the scalp and/or the hair. The same is true of the support, and also of the composition carried by the support.

The article according to the invention preferably does not contain any adhesive, but it can adhere to the skin when it is moistened.

This article is preferably flexible, i.e. supple. The term "supple" should be understood to mean an article that can be compressed or that can bend without breaking, and that can adjust to the contours of the human body. A supple article produced in the form of a fibrous sheet can, in certain examples of implementation, be folded over at least once without breaking into two pieces.

This article is generally preferably a single-use article.

Moreover, the article is preferably generally dry to the touch before use.

After the article has been manufactured, it can, for example, be packaged in bulk in a box, or in an individual packaging. Where appropriate, the articles are packaged as a string. The articles can also be folded over on themselves and intercalated, such that the withdrawal of an article brings the next one into a configuration that facilitates it being gripped.

Thus, a subject of the invention, according to another of its aspects, is also an assembly comprising:
  a packaging,
  at least one article as defined above.

The invention thus offers new possibilities for the packaging and the formulation of patches.

In an example of implementation of the invention, the article made up of the support and the composition containing the water-soluble gelling agent is intended to be brought into contact with water before it is used. The support is thus first completely solubilized before the article is applied to the human body. According to the amount of water added to the article in order to solubilize the support, the apparent viscosity of the patch obtained can be readily adjusted.

In another variant of implementation of the invention, the article made up of the support and the composition carried by the support is brought into contact with a region of the human body, for example the skin or the hair, before it is completely solubilized, or even before it is made wet. This may make it possible, for example, depending on the amount of water added, to modify the properties according to the desired result. Water can be poured onto the article although the latter is not in contact with the region of the body to be treated, or else the region of the body can also be moistened, or else water can be projected or poured onto the support while the article is in contact with the region to be treated.

According to a preferred method of use of the article according to the invention, the article is run under water and is applied to the area to be treated.

Support

The support is preferably in the form of a sheet comprising water-soluble fibres, i.e. fibres that are water-soluble at a temperature less than or equal to 30° C., preferably water-soluble at a temperature less than or equal to 20° C., i.e. having a temperature for dissolution in water ranging from more than 0° C. to 30° C., preferably from more than 0° C. to 20° C., and for example from 5° C. to 30° C., and better still from 5 to 20° C.

The support may have any shape and preferably has a shape suitable for the intended use, for example a rectangular, round or oval shape, and it preferably has dimensions that allow it to be gripped between at least two fingers. Thus, the support may have, for example, an ovoid shape approximately 2 to 10 cm long and approximately 0.5 to 4 cm wide, or a disc shape approximately 2 to 10 cm in diameter, or a square shape, the length of the sides being approximately 5 to 15 cm, or a rectangular shape approximately 5 to 15 cm long, it being understood that it may have any other shape and size suitable for the desired use.

The fibres of the support are generally entangled so as to form the sheet of fibres. As indicated above, the expression "sheet comprising water-soluble fibres" means a sheet that may consist entirely of water-soluble fibres or a sheet that may comprise both water-soluble fibres and water-insoluble fibres, there preferably being more soluble fibres than insoluble fibres. The sheet of fibres very preferably should comprise at least 60% by weight of soluble fibres, more preferably at least 70%, and better still at least 80% by weight relative to the total weight of the fibres. It can thus comprise, for example, more than 95% by weight, or even more than 99% by weight and even 100% by weight of water-soluble fibres relative to the total weight of the fibres of the support. Thus, the support may consist entirely of sheets of soluble fibres or it may consist of sheets comprising a mixture of soluble fibres and insoluble fibres, the insoluble fibres being, according to the definition of the present invention, fibres which are not water-soluble at a temperature less than or equal to 30° C. The fact of having insoluble fibres may make it possible to have a product with a thermal effect that at the same time is a scrub product, the insoluble fibres constituting the exfoliating compound.

Thus, the support can be formed from two sheets consisting of water-soluble fibres, or else from a sheet consisting of water-soluble fibres and a sheet comprising both soluble fibres and insoluble fibres, or alternatively also from a sheet consisting of water-soluble fibres and a sheet consisting of water-insoluble fibres, or else from two sheets comprising both soluble fibres and insoluble fibres. There may also be more than two sheets, each of which can independently comprise one or both of soluble fibres and insoluble fibres.

According to a preferred embodiment of the invention, the support is free of water-insoluble fibres and it is composed only of water-soluble fibres, such that it is entirely water-soluble.

The soluble fibres may be made of any soluble material that can be spun into fibres. Preferably, the water-soluble fibres are produced with polyvinyl alcohol (PVA) according to a process which gives them the desired solubility, it being possible for the PVA to have several degrees of polymerization.

PVA fibres that are water-soluble at a temperature less than or equal to 30° C. are marketed by the Japanese company Kuraray under the trade name Kuralon K-II WN2. The process for manufacturing these fibres comprises the preparation of a solution to be spun, by dissolution of a water-soluble PVA-based polymer in a first organic solvent, the spinning of the solution in a second organic solvent so as to obtain solidified filaments, and the wet drawing out of the filaments, from which the first solvent is removed, and which are then dried and subjected to a thermal treatment. The cross section of these fibres may be substantially circular. These fibres have a tensile strength of at least 2.7 g/dtex (3 g/d). Application EP-A-0 636 716 describes such PVA-based water-soluble fibres and the process for the manufacture thereof.

The invention is not limited to the use of PVA, and fibres made of other water-soluble materials can also be used, with the proviso that these materials dissolve in water having the desired temperature, for example polysaccharide fibres marketed under the name Lysorb by the company Lysac Technologies, Inc, or polyholoside polymer-based fibres such as glucomannan or starch.

The sheet of fibres can, where appropriate, comprise a mixture of various fibres that are water-soluble at different temperatures (up to 30° C.).

The fibres may be composites, and they may, for example, comprise a core and a sheath that are not of the same nature, for example formed from various grades of PVA.

When the sheet of fibres contains insoluble fibres, the latter can be made of any material useful as insoluble fibres; this may be, for example, fibres made from silk, cotton, wool, flax, cellulose extracted in particular from wood, vegetables or algae, polyamide (Nylon®), polylactic acid, modified cellulose (rayon, viscose, acetate, in particular rayon acetate), poly-p-phenyleneterephthalamide, in particular Kevlar®, acrylic, in particular poly(methyl methacrylate) or poly(2-hydroxyethyl methacrylate), polyolefin, and in particular polyethylene or polypropylene, glass, silica, aramide, carbon, in particular in graphite form, Teflon®, insoluble collagen, polyesters, polyvinyl chloride or polyvinylidene chloride, polyvinyl alcohol, polyacrylonitrile, chitosan, polyurethane, polyethyleneterephthalate, fibres formed from a mixture of the compounds mentioned above, such as polyamide/polyester fibres or viscose/polyester fibres. Nonwovens are described, in general, in Riedel "Nonwoven Bonding Methods & Materials", Nonwoven World (1987), incorporated herein by way of reference.

In a specific example of implementation of the invention, the support sheet is a nonwoven comprising water-soluble fibres, alone or as a mixture with insoluble fibres as indicated above, with at most 40% by weight of insoluble fibres relative to the total weight of the fibres forming the sheet. Preferably, the nonwoven consists of water-soluble fibres, i.e. it does not contain insoluble fibres.

The support may be substantially non-retractable once wet.

When the support comprises only one sheet of fibres, the composition containing the gelling agent can be deposited on the two faces of the support or on a single face, it being possible for the other face of the support to then be used, for example, for gripping the article.

When the support according to the present invention comprises two sheets, they may in a preferred embodiment be two sheets of nonwoven, it being possible for all the embodiments described below to be used, it being possible for the sheets to contain or not contain insoluble fibres, and it even being possible for one of the sheets to consist only of insoluble fibres, provided that the other sheet contains soluble fibres.

According to a specific embodiment of the invention, each of the sheets is a nonwoven consisting of fibres that are soluble at a temperature less than or equal to 30° C., i.e. the sheets contain only water-soluble fibres.

According to another embodiment, one of the sheets is entirely water-soluble and is a nonwoven consisting of fibres that are soluble at a temperature less than or equal to 30° C., and the other sheet is insoluble and is a nonwoven consisting of insoluble fibres.

According to yet another embodiment, the support comprises two sheets containing soluble or partially soluble fibres with at most 40% of insoluble fibres, and, in addition, a sheet consisting of insoluble fibres, constituting an insoluble substrate. Thus, the support may comprise at least one layer of a water-insoluble substrate, i.e. a substrate comprising only insoluble fibres. In a specific example of this embodiment, the support comprises a soluble sheet of a nonwoven consisting of fibres that are water-soluble at a temperature less than or equal to 30° C., and an insoluble sheet of a nonwoven consisting of water-insoluble fibres.

A multilayer structure with at least one layer formed from a water-insoluble substrate can, for example, be of use for producing an article comprising a support in the shape of a fingerstall. The layer formed from water-soluble fibres is located on the outside of the article, intended to solubilize during use, after having been moistened or upon coming into contact with a moistened region of the body.

All the appropriate techniques for constituting a nonwoven from fibres can be used to manufacture the sheets made of nonwoven, regardless of whether they are soluble or insoluble. For example, the fibres can be formed by extrusion and deposited on a conveyor to form a sheet of fibres which is then consolidated by means of a standard fibre bonding technique, for instance needle bonding, hot-bonding, calendering or air-through bonding, in which technique the sheet passes through a tunnel in which hot air is blown. The latter technique is advantageously used when the sheet consists of two-component fibres, for example fibres comprising at least two grades of polyvinyl alcohol (PVA), the melting points or softening points of which are different, these fibres being, for example, co-extruded such that the fibre consists of at least a first grade located at the core of the fibre and of at least a second grade located at the periphery of the fibre, in the form of a sheath. The bonding of the fibres may be facilitated when the sheath has a melting point lower than that of the core.

The sheet of fibres may also be formed by carding fibres cut to a length of 10 to 50 mm, followed by deposition of the fibres on a conveyor where the sheet may then be consolidated by means of a bonding technique as described above.

When the support comprises several layers, regardless of whether or not all of the latter are made of water-soluble fibres, the various layers can be assembled in many ways, for example by seeding, bonding or sewing, and these layers can, where appropriate, consist of one or more cavities containing one or more cosmetic or dermatological compositions or several components of the same cosmetic composition to be mixed extemporaneously. When assembly is by sewing, a thread which is itself water-soluble may be used, where appropriate.

When the support comprises several sheets of nonwoven, the latter may be assembled in particular by heat-sealing at their periphery so as to constitute a cushion capable of retaining, in an inner cavity, a composition containing the gelling agent.

According to another aspect of the invention, the support is free of adhesive, in particular of pressure-sensitive adhesive.

The density of the support may depend on the applications. The support may, for example, have a density of less than or equal to 0.1 g/cm$^3$ or else greater than 0.1 g/cm$^3$. According to a preferred embodiment of the invention, the support has a density of less than or equal to 0.1 g/cm$^3$, better still ranging from 0.01 g/cm$^3$ to 0.1 g/cm$^3$, which makes it possible to have a very aerated support which, as a result, dissolves more readily in water.

The composition containing at least one water-soluble gelling agent represents between 10 and 1000 W by weight, relative to the weight of the support, and preferably between 10 and 500% by weight, relative to the weight of the support, the expression "weight of the support" here being intended to mean the weight of the support alone, without the weight of the composition containing the water-soluble gelling agent. If the composition contains only the water-soluble gelling agent, it is this which can represent between 10 and 1000% by weight relative to the weight of the support, and preferably between 10 and 500% by weight relative to the weight of the support.

Water-Soluble Gelling Agents

The composition carried by the support contains one or more water-soluble gelling agents which swell in less than 30 seconds in water at a temperature of 20° C. to 30° C. The gelling agents contained in the composition carried by the support can be chosen in particular from polysaccharides which swell in less than 30 seconds in water at a temperature of 20° C. to 30° C., in particular gums which swell in less than 30 seconds in water at a temperature of 20° C. to 30° C., modified starches, and mixtures thereof.

The expression "water-soluble gelling agents which swell in less than 30 seconds in water at a temperature of 20° C. to 30° C." means gelling agents which dissolve or swell readily in water at a temperature less than 30° C., ranging, in particular, from 20° C. to 30° C., and at a concentration of from 5% to 50% by weight, so as to give a viscous gel that does not run.

As water-soluble gelling agents, mention may in particular be made of karaya gum, konjac gum, modified starches, and mixtures thereof.

As modified starches, mention may, for example, be made of those derived from maize starch, rice starch, cassava starch, potato starch, wheat starch, sorghum starch, pea starch, and mixtures thereof. Among modified starches, mention may be made of precooked starches, hydrolysed starches, crosslinked starches, for example crosslinked with a methylolurea derivative or with octenylsuccinic anhydride or else with epichlorohydrin, esterified starches, etherified starches, oxidized starches, refined starches, starches roasted in the presence of an acid, or else grafted starches, for example grafted with sodium polyacrylates, coated starches, for example coated with amino acids, and/or mixtures thereof.

Among the modified starches that are particularly suitable for the invention, mention may be made of:

that sold under the names Structure XL and Structure Zea (hydroxypropyl starch phosphate) by the company National Starch;

the pregelatinized modified maize starch and potato starch sold, respectively, under the names Novation 5600 and 6600, by the company National Starch;

the modified maize starches sold under the names Ultra-tex 1, 2, HV, 2000, by the company National Starch;

the starches sold under the names Sanfresh ST-100C, ST100MC, IM-300MC (INCI name sodium polyacrylate starch) by the company Sanyo Chemical Industries;

hydrolysed starches grafted with acryloacrylamide/sodium acrylate copolymer (INCI name: starch/acrylamide/sodium acrylate copolymer), such as those sold under the names Water Lock A-240, A-180, B-204, D-223, A-100, C-200, D-223 and G-400 by the company Grain Processing, and mixtures thereof.

The amount of water-soluble gelling agent in the composition can range, for example, from 5 to 100% by weight, better still from 10 to 100% by weight, and even better still from 20 to 100% by weight relative to the total weight of the composition.

Compositions

The compositions carried by the support and containing the water-soluble gelling agent(s) are preferably anhydrous compositions. They are preferably in pulverulent or pasty form, and more preferably in pulverulent form. They are compositions suitable for topical application, in particular cosmetic or dermatological compositions.

Thus, the compositions that can be used in the invention may be, for example:

lyophilized or atomized emulsions, such as those described in document FR-A-2,727,312 or those based on modified starch, described in document EP-A-0 938 892. These emulsions are obtained by lyophilizing or atomizing an O/W emulsion containing a pulverulent phase, producing milks or creams by mixing with water when they are used.

foaming compositions in the form of powders, containing pulverulent surfactants, such as those based on starch that are described in document EP-A-0 925 777, producing foam by mixing with water when they are used.

exfoliating compositions containing scrubs or exfoliating particles.

compositions formed by simple mixing of the constituents, the latter preferably being in powdered form.

The composition is preferably anhydrous but may optionally contain a certain amount of water at the time it is impregnated onto the support. However, so as to avoid premature solubilization thereof, the water introduced onto the support during its impregnation preferably is removed, for instance by heating. Moreover, the composition may contain a certain amount of water, which is generally bound water and which may come in particular from the hygroscopic starting materials that contain water, such as starches. The final amount of water in the composition present on the article is preferably a maximum of 20% by weight, and more preferably a maximum of 10% by weight, including 15, 12, 8, 6, 4, 2 and 0% by weight, relative to the total weight of the composition.

In the case of a coloured composition, the article may be packaged in a packaging comprising, where appropriate, a coloured control representative of the colour of the composition obtained after dissolving the article, in order to inform the consumer before purchase.

When the composition is such that it is to be deposited on the support by the user himself or herself, the composition and the support can be provided in the form of a kit, for example. The composition is, for example, provided in sufficient amount for it to be possible to distribute a plurality of doses thereof on a set of supports intended to be used successively.

Additives

The composition carried by the support can contain, depending on the final use of the article, compounds other than the water-soluble gelling agents.

These additives can in particular be anhydrous or in solid form (powder). They can in particular be chosen from those generally used in the cosmetics and dermatological fields, such as, for example, surfactants, sequestering agents, fragrances, antioxidants, active agents, preserving agents, dyestuffs (such as hydrophilic pigments and dyes) and inorganic fillers and/or organic fillers such as exfoliating particles and kaolin. These adjuvants and also the amounts thereof must be such that they do not modify the property desired for the composition of the invention. According to one specific embodiment of the invention, these additives may be encapsulated or adsorbed onto powders.

The surfactants may in particular be foaming surfactants. As foaming surfactants, use may be made of those normally used in the cosmetics field, it being possible for these surfactants to be anionic, nonionic, cationic, amphoteric or zwitterionic.

The total amount of foaming surfactant(s) may range, for example, from 2 to 80% by weight, preferably from 10 to 70% by weight, and better still from 10 to 50% by weight relative to the total weight of the composition.

As foaming anionic surfactants, mention may be made, for example, of fatty acid salts that constitute soaps and that are derived from a fatty acid having an alkyl chain containing from 6 to 22 carbon atoms, preferably from 8 to 18 carbon atoms; alkyl sulphates and alkyl ether sulphates; sulphonates; alkali metal salts of N-acylamino acids, such as sarcosinates, alaninates, glutamates, aspartates, glycinates; and mixtures thereof.

As nonionic surfactants, mention may, for example, be made of sugar esters, sugar ethers such as alkyl polyglucosides (APGs), condensates of alkylene oxides and of alkylphenols, ethers of a fatty alcohol and of polyols, and mixtures thereof.

As amphoteric or zwitterionic surfactants, mention may be made of betaines and derivatives thereof, sultaines and derivatives thereof, imidazolinium derivatives, and mixtures thereof.

The preferred surfactants are those in powdered form, such as, for example, sodium lauryl sulphate, for instance the product sold under the name Empicol LZ D by the company Allbright & Wilson or under the name Tensopol USP97 by the company Tensachem; cocamidopropylbetaine, for instance the product sold under the name Tegobetain CK D by the company Degussa; sodium lauroyl glutamate, for instance the product sold under the name Amisoft LS 11 by the company Ajinomoto; monosodium myristoyl glutamate, for instance the product sold under the name Acylglutamate MS 11 by the company Ajinomoto; the mixture of sodium laureth sulphate and silica, sold under the name Texapon KE 2713 by the company Cognis; disodium cocamido MEA-sulphosuccinate, for instance the product sold under the name Mackanate CM 100 by the company MacIntyre; sodium methyl cocoyl taurate, for instance the product sold under the name Tauranol WSP by the company Finetex; sodium decyl d-galactoside uronate, for instance the product sold under the name Decyl d-galactoside uronate de sodium by the company Ard-Soliance; the lauroyl methyl beta-alanine (acid form) sold under the name LMA-H by the company Mitsui Toatsu; the n-lauroyl-n-hydroxyethyl-beta-alanine sold under the name LHEA by the company Mitsui Toatsu; the sodium cocoyl glycinate sold under the name Amilite GCS-11(F) by the company Ajinomoto; sodium cocyl isethionate, for instance the product sold under the name Jordapon CI P by the company BASF; sodium lauryl sulphoacetate, for instance the product sold under the name Lathanol LAL poudre [powder] by the company Stepan; potassium myristate, for instance the product sold under the name Myristate de potassium (DUB MK) by the company Stearinerie Dubois; potassium laurate, for instance the product sold under the name Laurate de potassium (DUB LK) by the company Stearinerie Dubois, and sucrose laurate, for instance the product sold under the name Grilloten LSE 87 by the company Degussa.

The active agents can be chosen in particular from keratolytic agents, moisturizers, soothing agents and antimicrobial agents.

As moisturizers, mention may be made of polyols such as glycerol; compounds that act on the barrier function, with a view to maintaining moisturization of the stratum corneum, or occlusive compounds, in particular ceramides, sphingoid-based compounds, lecithins, glycosphingolipids, phospholipids, cholesterol and its derivatives, phytosterols (stigmasterol, β-sitosterol, campesterol), essential fatty acids, 1,2-diacylglycerol, 4-chromanone, pentacyclic triterpenes such as ursolic acid, petroleum jelly and lanolin; compounds that directly increase the water content of the stratum corneum, such as threalose and its derivatives, hyaluronic acid and its derivatives, glycerol, pentanediol, sodium pidolate, serine, xylitol, sodium lactate, poly(glycerol acrylate), ectoin and its derivatives, chitosan, oligosaccharides and polysaccharides, cyclic carbonates, N-lauroylpyrrolidonecarboxylic acid, and N-α-benzyl-L-arginine; and mixtures thereof.

As keratolytic agents, mention may be made of β-hydroxy acids, in particular salicylic acid and its derivatives (including 5-n-octanoylsalicylic acid); α-hydroxy acids, such as glycolic acid, citric acid, lactic acid, tartaric acid, malic acid or mandelic acid, and mixtures thereof.

As soothing agents that can be used in the composition according to the invention, mention may, for example, be made of pentacyclic triterpenes and extracts of plants (for example: *Glycyrrhiza glabra*) containing same, for instance β-glycyrrhetinic acid and salts thereof and/or derivatives thereof (glycyrrhetinic acid monoglucuronide, stearyl glycyrrhetinate, 3-stearoyloxyglycyrrhetic acid), ursolic acid and salts thereof, oleanolic acid and salts thereof, betulinic acid and salts thereof, extracts of plants such as *Paeonia suffruticosa* and/or *lactiflora, Laminaria saccharina, Boswellia serrata, Centipeda cunnighami, Helianthus annuus, Linum usitatissimum, Cola nitida, Epilobium Angustifolium, Aloe vera, Bacopa monieri*, salicylic acid salts, and in particular zinc salicylate, canola oil, bisabolol and extracts of camomile, allantoin, Sepivital EPC (phosphoric diester of vitamin E and C) from Seppic, omega-3 unsaturated oils such as musk rose oil, blackcurrant oil, ecchium oil or fish oil, plankton extracts, capryloylglycine, Seppicalm VG (sodium palmitoylproline and *Nymphea alba*) from Seppic, tocotrienols, piperonal, an extract of clove, phytosterols, cortisone, hydrocortisone, indomethacin and betamethasone.

As antimicrobial agents, mention may, for example, be made of 2,4,4'-trichloro-2'-hydroxydiphenyl ether (or triclosan), 3,4,4'-trichlorocarbanilide (or triclocarban), phenoxyethanol, phenoxypropanol, phenoxyisopropanol, hexamidine isethionate, metronidazole and its salts, miconazole and its salts, itraconazole, terconazole, econazole, ketoconazole, saperconazole, fluconazole, clotrimazole, butoconazole, oxiconazole sulphaconazole, sulconazole, terbinafine, ciclopiroxe, ciclopiroxolamine, undecylenic acid and its salts, benzoyl peroxide, 3-hydroxybenzoic acid, 4-hydroxybenzoic acid, phytic acid, N-acetyl-L-cysteine acid, lipoic acid, azelaic acid and its salts, arachidonic acid, resorcinol, octopirox, octoxyglycerol, octanoylglycine, caprylyl glycol, 10-hydroxy-2-decanoic acid, dichlorophenyl imidazole dioxolane and its derivatives described in patent WO-A-93/18743, farnesol, phytosphingosines, and mixtures thereof.

Vitamins that may be used include water-soluble or liposoluble vitamins or provitamins, such as, for example, vitamin A (retinol), vitamin C (ascorbic acid), vitamin B3 or PP (niacinamide), vitamin B5 (panthenol), vitamin B6 or pyridoxine, vitamin E (tocopherol), vitamin K1, beta-carotene, and the derivatives of these vitamins, and in particular esters thereof, and mixtures thereof.

The composition may also contain exfoliants, in particular for constituting an exfoliating composition or a facial scrub or body scrub. As exfoliants, mention may, for example, be made of exfoliating or scrubbing particles of inorganic, plant or organic origin.

The composition according to the invention may also contain one or more lipophilic compounds, fatty substances and, in particular, oils, or oily active agent, provided that these lipophilic compounds do not disturb the swelling of the gelling agent. If they are present, the fatty substances can constitute up to 50% of the composition carried by the support, for example from 0 to 50% by weight, preferably from 0.1 to 40% by weight, better still from 0.1 to 20% by weight, and even better still from 0.5 to 10% by weight relative to the total weight of the composition. These lipophilic compounds may contribute to having an article that can be more readily rinsed off.

Of course, those skilled in the art would take care to choose this or these possible additive(s) and/or the amount(s) thereof in such a way that the advantageous properties intrinsically associated with the composition in accordance with the invention are not, or not substantially, impaired by the addition(s) envisaged.

The article according to the invention constitutes in particular a patch, and it can be used as a composition for cleansing and removing makeup from the skin, for the treatment of signs of ageing, for the treatment of greasy skin, for moisturizing the skin, for scrubbing the skin, for sun protection and aftersun treatment, and for the treatment of sensitive or sensitized skin.

The article according to the invention can constitute in particular a rinse-off patch or a rinse-off two-in-one article for the specific treatment of a restricted area, or as a single-dose product to be applied to a larger area, having moistened the product beforehand.

It is generally used by moistening the area to be treated and applying the patch thereto, the patch converting into a gel, and then removing it by simply rinsing.

The article according to the invention may find applications in care in general, for example for cleansing and removing makeup from the skin, for the treatment of signs of ageing, for the treatment of greasy skin, for moisturizing the skin, for scrubbing the skin (including peelings), for sun protection and aftersun treatment, and also for the treatment of sensitive or sensitized skin.

The article according to the invention may in particular constitute a cleansing product for the skin, an exfoliating product or a skin care product.

The examples which follow serve to illustrate the invention without, however, being limiting in nature. The amounts are indicated as % by weight unless otherwise mentioned, and they correspond, unless otherwise mentioned, to the amount of starting material and not to the amount of active material. The names of the compounds used are given as the CTFA name, as the chemical name or as the trade name.

EXAMPLES

The article used in the examples is prepared with a support made of PVA-based Kuralon K-II WN2 fibres. It is obtained by heat-sealing, at their periphery, two layers having a weight of 80 g/m². The article is in the form of a disc 3 cm in diameter, comprising a cavity into which is introduced the composition in an amount of approximately 0.3 grams.

|  | Example 1 according to the invention | Comparative example | Example 2 according to the invention | Example 3 according to the invention |
|---|---|---|---|---|
| Modified starch (1) | 100 | — | 80 | — |
| Polyacrylate-grafted starch (2) | — | — | — | 69 |
| AMPS polymer | — | 100 | — | — |
| Glycolic acid | — | — | 20 | — |
| Kaolin | — | — | — | 10 |
| Triclosan | — | — | — | 1 |
| Sodium lauroyl glutamate (4) | — | — | — | 20 |

(1) Structure XL (National Starch)
(2) Sanfresh ST-100C (Sanyo Chemical Industries)
(3) Hostacerin AMPS (Clariant)
(4) Aminosoft LS11 (Ajinomoto)

The examples were obtained by mixing the powders, and then by introducing approximately 0.3 grams of the mixture into the cavity of the support, which was then closed by sealing.

For all the examples, the article is moistened beforehand with an amount of water greater than or equal to 2 ml, before being applied to the area to be treated. In the 3 examples according to the invention, a gel is obtained in less than 30 seconds, whereas the comparative example gives a fluid solution.

The patch of Example 2 constitutes a peeling: after the addition of approximately 2 ml of water, it is applied to the skin, and it is then rinsed off after a leave-on time of approximately 5 minutes.

The patch of Example 3 constitutes a care for greasy skin to be rinsed after application. It can be used as a concentrated care to be applied to the area of the nose for 5 minutes after having been rehydrated with approximately 2 ml of water, or as a daily cleansing product after dilution with a larger amount of water (more than 4 ml of water).

The above written description of the invention provides a manner and process of making and using it such that any person skilled in this art is enabled to make and use the same, this enablement being provided in particular for the subject matter of the appended claims, which make up a part of the original description and including an article, in particular a cosmetic or dermatological article, comprising a support in the form of at least one sheet comprising fibres that are water-soluble at a temperature less than or equal to 30° C., and a composition carried by the support, containing at least one water-soluble gelling agent which swells in less than 30 seconds in water at a temperature of 20° C. to 30° C.

As used herein, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A process for treating a keratin material, comprising:
dissolving in water a support in the form of at least one sheet comprising fibres that are water-soluble at a temperature of 0-30° C. and a composition carried by the support comprising at least one water-soluble gelling agent which swells in less than 30 seconds in water at a temperature of 20° C. to 30° C. to form a resultant composition; and
applying the resultant composition to the keratin material.

2. The process of claim 1, wherein the fibres that are water-soluble at a temperature less than or equal to 30° C. are prepared with polyvinyl alcohol.

3. The process according to claim 1, wherein the at least one sheet comprising fibres that are water-soluble is a nonwoven.

4. The process according to claim 1, wherein the at least one sheet comprising fibres that are water-soluble further comprises water-insoluble fibres.

5. The process according to claim 1, wherein the amount of water-insoluble fibres is at most 40% by weight relative to the total weight of the fibres.

6. The process according to claim 1, wherein the support comprises at least two sheets, at least one of which comprises fibres that are water-soluble at a temperature of 0-30° C.

7. The process according to claim 6, wherein the support in the form of at least two sheets that together define one or more cavities, at least one of the sheets comprising fibres that are water-soluble at a temperature of 0-30° C., and
the cavity comprising the composition comprising a water-soluble gelling agent which swells in less than 30 seconds in water at a temperature of 20° C. to 30° C.

8. The process according to claim 7, wherein at least two of the sheets of fibres are nonwovens.

9. The process according to claim 7, wherein one of the sheets is a nonwoven consisting of fibres that are water-soluble at a temperature of 10-7° C., and another of the sheets is a nonwoven consisting of water-insoluble fibres.

10. The process according to claim 7, wherein the at least two sheets are assembled at their periphery.

11. The process according to claim 10, wherein the sheets are heat-sealed.

12. The process according to claim 7, wherein the support is entirely water-soluble.

13. The process according to claim 7, wherein the amount of water-soluble gelling agent ranges from 5 to 100% by weight relative to the total weight of the composition.

14. The process according to claim 1, wherein the gelling agent comprises at least one of karaya gum, konjac gum, modified starches, and mixtures thereof.

15. The process according to claim 1, wherein the composition carried by the support represents between 10 and 1000% by weight relative to the weight of the support.

16. The process according to claim 1, wherein the composition carried by the support further comprises at least one compound selected from the group consisting of foaming surfactants, polymers, lipophilic compounds, exfoliants, active agents, and mixtures thereof.

17. The process according to claim 1, wherein the resultant composition constitutes an article for cleansing or removing makeup from the skin, for the treatment of signs of ageing, for the treatment of greasy skin, for moisturizing the skin, for scrubbing the skin, for sun protection and antisun treatment, or for the treatment of sensitive or sensitized skin.

18. The process according to claim 1, wherein the support is entirely water-soluble.

19. A process for treating a keratin material with a cosmetic or dermatological active, comprising:

dissolving in water a support in the form of at least one sheet comprising fibres that are water-soluble at a temperature of 0-30° C. and a composition carried by the support comprising at least one water-soluble gelling agent which swells in less than 30 seconds in water at a temperature of 20° C. to 30° C. in water with a cosmetic or dermatological active to form a resultant composition; and applying the resultant composition to the keratin material to treat the keratin material with the cosmetic or dermatological active.

* * * * *

UNITED STATES PATENT AND TRADEMARK OFFICE
CERTIFICATE OF CORRECTION

| | | |
|---|---|---|
| PATENT NO. | : 7,811,953 B2 | Page 1 of 1 |
| APPLICATION NO. | : 12/169779 | |
| DATED | : October 12, 2010 | |
| INVENTOR(S) | : Odile Aubrun-Sonneville | |

It is certified that error appears in the above-identified patent and that said Letters Patent is hereby corrected as shown below:

Column 14, line 60, "10-7°C" should read --0-30°C--.

Signed and Sealed this
Twenty-fifth Day of January, 2011

David J. Kappos
*Director of the United States Patent and Trademark Office*